United States Patent [19]

Trivedi et al.

[11] 4,270,983
[45] Jun. 2, 1981

[54] LIQUID-LIQUID EXTRACTION OF ISOBUTYRIC ACID FROM AQUEOUS HF SOLUTIONS THEREOF

[75] Inventors: Bhupendra C. Trivedi, Worthington; Dace Grote; Thomas O. Mason, both of Columbus, all of Ohio

[73] Assignee: Ashland Oil, Inc., Ashland, Ky.

[21] Appl. No.: 118,359

[22] Filed: Feb. 4, 1980

[51] Int. Cl.³ .................... C07C 51/44; C07C 51/48
[52] U.S. Cl. ...................................... 203/43; 562/521
[58] Field of Search .................................. 203/43–46, 203/95; 562/521

[56] References Cited

U.S. PATENT DOCUMENTS

| | | | |
|---|---|---|---|
| 2,831,877 | 4/1958 | Koch | 562/521 |
| 3,282,993 | 11/1966 | Chafetz et al. | 562/521 |
| 3,632,638 | 1/1972 | Hyman | 562/521 |
| 3,663,613 | 5/1972 | Pai et al. | 562/521 |
| 3,816,496 | 6/1974 | Schnabel | 203/43 |

FOREIGN PATENT DOCUMENTS 1174209  12/1969  United Kingdom ............... 562/521

Primary Examiner—Wilbur L. Bascomb, Jr.
Attorney, Agent, or Firm—William Kammerer

[57] ABSTRACT

A method for recovering isobutyric acid from a solution thereof in concentrated aqueous hydrogen fluoride, the latter having served as the reaction medium for effecting the carbonylation of propylene. The method features the partial removal of anhydrous hydrogen fluoride from said solution to provide an aqueous phase of reduced hydrogen fluoride content from whence the isobutyric acid is extracted with optimum efficiency with an immiscible organic solvent.

4 Claims, 2 Drawing Figures

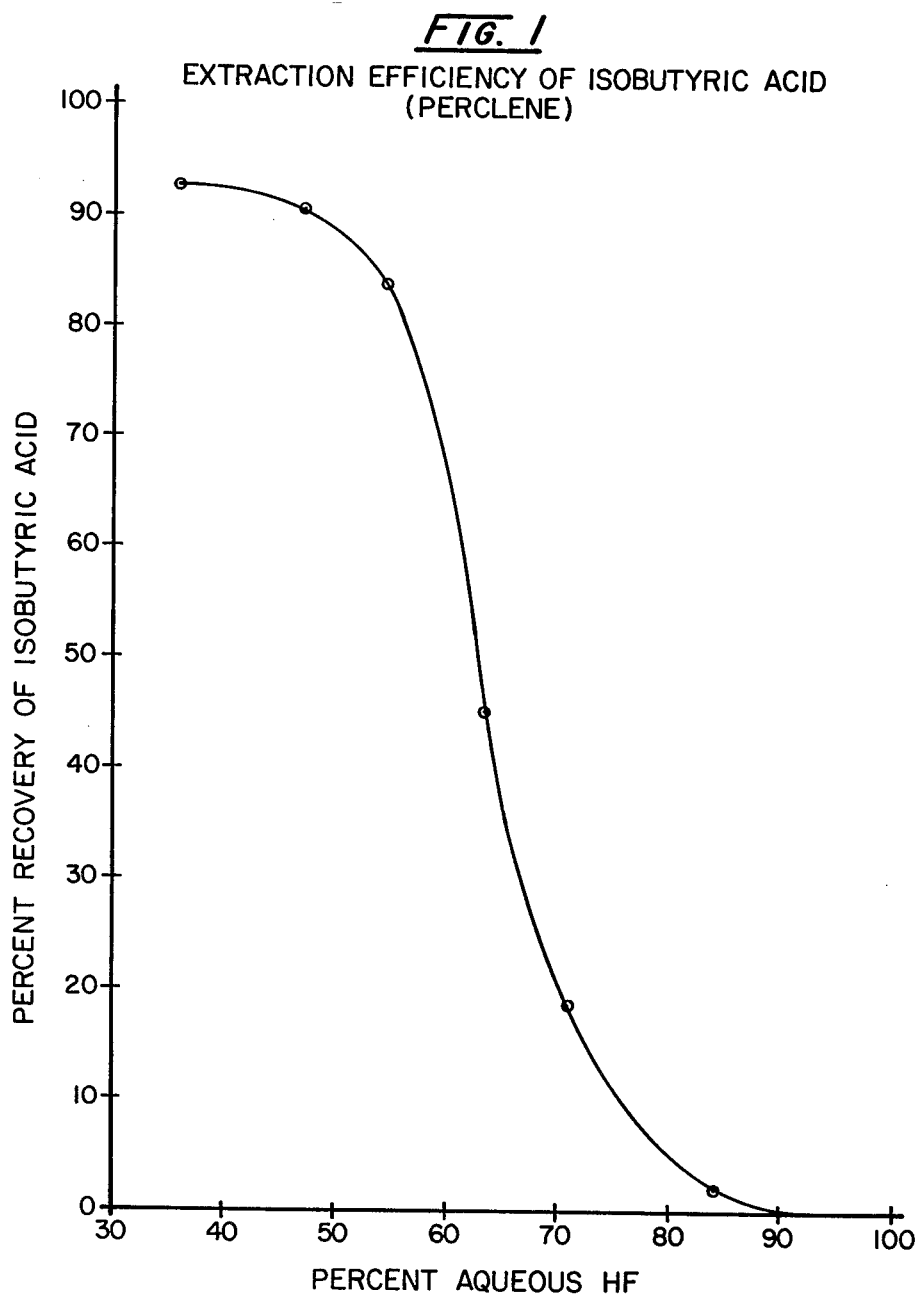

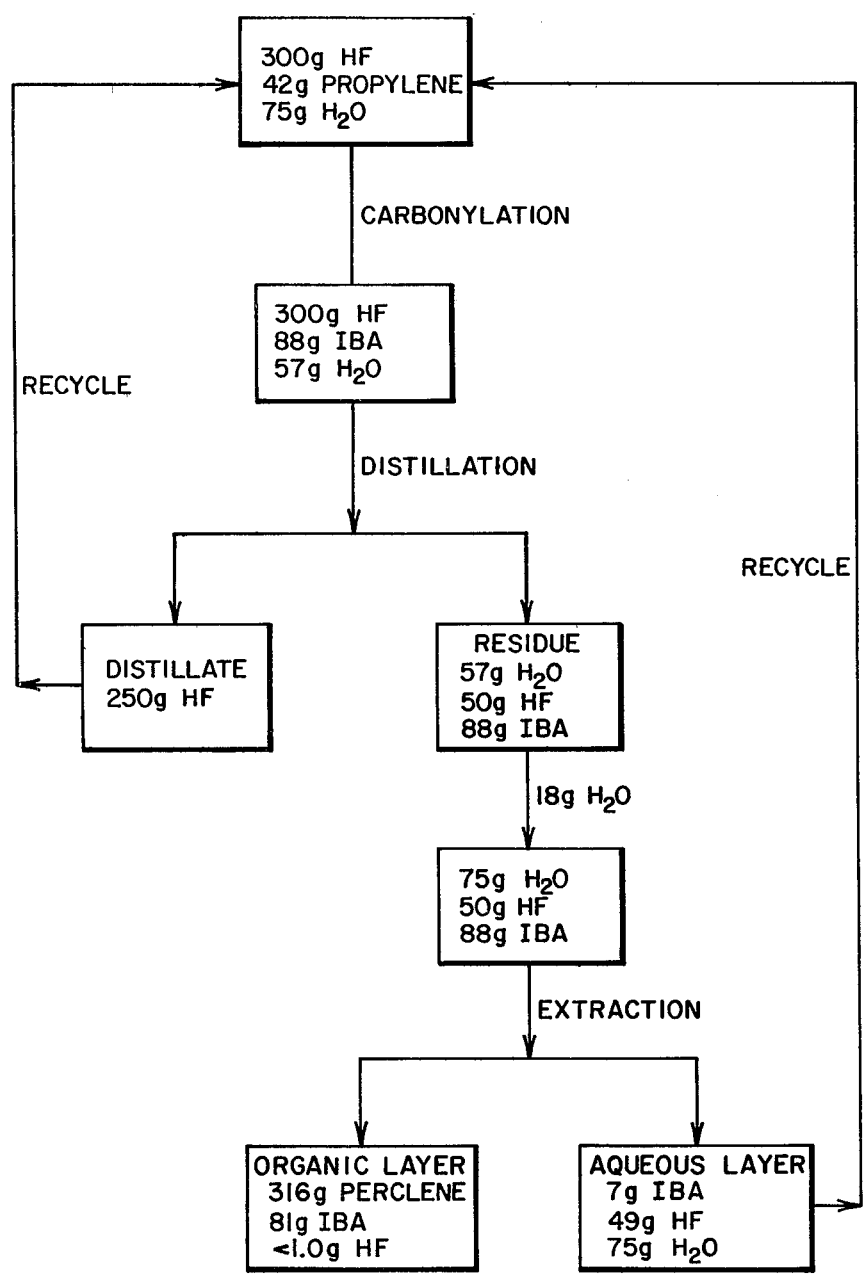

LIQUID-LIQUID EXTRACTION OF ISOBUTYRIC ACID FROM AQUEOUS HF SOLUTIONS THEREOF

BACKGROUND OF THE INVENTION

1. Field of the Invention

This invention relates to a method for separating isobutyric acid from an aqueous hydrogen fluoride solution thereof by a liquid-liquid extraction procedure.

2. Description of the Prior Art

It is known that olefins react rapidly with carbon monoxide at low temperatures and under moderate pressure in the presence of a strong acidic media, typically representative of which is anhydrous hydrogen fluoride, concentrated sulfuric acid and anhydrous chlorosulfonic acid. The postulated carbonylation mechanism involved is conventionally referred to as the Koch reaction and is exemplified in U.S. Pat. No. 2,831,879. The reaction reportedly provides a good yield of acids only when butene or a higher olefin is used. In the case of propylene, the formation of by-products is indicated to be rampant and an exceedingly lower reaction temperature is taught as being required in order to obtain yields on the order of that observed in utilizing the higher olefins.

Noting the relative ineffectiveness of the Koch reaction for carbonylating propylene, subsequent investigators, Takezaki et al, undertook to study the use of aqueous hydrogen fluoride (HF) in order to improve yields of isobutyric acid. Their findings are given in Bull. Jap. Pet. Inst., 8, 31–38 (1966) wherein it is reported that optimum operating conditions, including the use of 80% HF-20% $H_2O$ as the reaction medium, provided a commercially acceptable yield of isobutyric acid.

While yield of product is very important for any commercial undertaking, an equally important consideration in this instance is that the substantial amount of HF required for effecting the reaction must be recovered essentially in toto for recycling. Moreover, it must be readily recoverable in about an 80% aqueous form as employed in the reaction.

Komatsu et al, Bull. Jap. Pet. Inst., 16, 124–131 (1974) addresses this recovery aspect as it specifically applies to the Koch reaction employing a lower olefin. A procedure is accordingly outlined therein for the recovery of HF following the preparation of pivalic acid in accordance with the Koch reaction. Essentially the procedure involves hydrolyzing the carbonylation reaction mixture with 53% aqueous HF and distilling to recover anhydrous HF. Thereupon the residue in the form of an equimolar HF complex of pivalic acid is hydrolyzed using a minimum amount of water to provide two layers; the top layer being the carboxylic acid product and the other being recyclable 50% aqueous HF.

However, the foregoing procedure is not applicable to the preparation of isobutyric acid in 80% aqueous HF for a combination of factors. For one, said carboxylic acid forms directly in accordance with this reaction and exhibits complete solubility in the aqueous HF medium. Secondly, 35% aqueous HF represents a constant boiling mixture in which isobutyric acid still remains soluble. Accordingly, one is constrained to distill the reaction mixture to recover as much HF as possible then dilute with a substantial amount of water to effect phase separation. The diluted HF solution can of course be concentrated by distillation to provide the 35% aqueous HF for recycling. But such a recovery method would be too tedious and energy intensive to be practical.

SUMMARY OF THE INVENTION

In accordance with the present invention, a method is provided for recovering isobutyric acid from a reaction mixture resulting from the carbonylation of propylene in 80% aqueous hydrogen fluoride, with the concomitant recovery in a facile manner of the HF for reuse purposes. The contemplated carbonylation reaction results in a solution of said carboxylic acid in about 84% aqueous HF as a portion of the water initially present is consumed in the underlying reaction. The reaction mixture is initially distilled to recover anhydrous HF which is readily separated until the constant boiling 35% aqueous HF solution is obtained. Upon removing anhydrous HF to the extent of providing 60% or a lower concentration of HF based on the aqueous portion of the residue, the residue is contacted with an immiscible organic solvent to effect the liquid-liquid extraction of the isobutyric content thereof.

BRIEF DESCRIPTION OF THE DRAWINGS

FIG. 1 graphically illustrates the general relationship between the HF content of an aqueous HF solution of isobutyric acid and the corresponding efficiency of liquid-liquid extraction for recovery of the carboxylic acid content.

FIG. 2 is block diagram schematically illustrating the implementation of the present invention to recover isobutyric acid from a solution thereof in concentrated aqueous HF resulting from the carbonylation of propylene in said media. The schematic additionally illustrates the facile recovery of HF for recycling afforded by the invention.

DETAILED DESCRIPTION OF THE INVENTION

As mentioned, the Takezaki et al article cited hereinbefore describes the optimum conditions for effecting the carbonylation of propylene in an aqueous HF medium. The preferred reaction medium is a solution of 80% HF and 20% water. For the sake of convenience, this mixture is referred to herein as 80% aqueous HF. Other relative proportions of HF to water are designated in a like manner. Applicable reaction temperatures are 90°–94° C. Lower temperatures can be used necessitating longer reaction times. Reaction temperatures in excess of 94° C., however, are to be avoided because such temperatures are prone to cause polymerization of the propylene. While the aqueous HF is conventionally referred to as the catalyst, the amounts thereof called for in effecting the reaction are relatively substantial. For best results the charge mole ratio of HF to propylene should be in excess of 10 and preferably in the order of 15. Total reaction pressure broadly applicable is from 70–340 atmospheres and more preferably on the order of about 200 atmospheres. Employing the optimum reaction conditions noted, one can readily realize a selectivity to isobutyric acid of 98% or higher in a reaction time span of 40 to 60 minutes.

FIG. 1 perhaps best illustrates the concept behind this invention and consequently will be discussed initially. As can be noted, the figure graphically portrays the efficiency of extracting isobutyric acid (IBA) from an aqueous HF solution thereof as a function of the HF concentration of the solution upon neglecting the IBA content. The immiscible organic solvent utilized to develop this data was perchloroethylene (PERCLENE) which was chosen because of its almost nil capacity to extract HF. A plurality of other solvents are useful for this purpose, all capable of extracting IBA to the extent exhibited by perchloroethylene. A further discussion concerning applicable extractants will be given later on.

The data for the plot of FIG. 1 was obtained from synthetic mixtures of the IBA in aqueous HF. The starting point was the hypothetical reaction product resulting from the carbonylation of propylene employing a molar ratio of HF to propylene of 15, using 80% aqueous HF and assuming a 100% selectivity to the formation of IBA. Other synthetic mixtures were accordingly prepared, each having a composition which would be provided by distilling progressively larger amounts of HF from the starting reaction mixture. The HF content of these synthetic mixtures, again, neglecting the IBA content thereof, are noted in the abscissa. The various synthetic mixtures were contacted with an equal volume of perchloroethylene in a single extraction whereupon the IBA content of the organic phase was determined in each instance. The percent recovery of IBA is noted on the ordinate of the graph thus showing the extraction efficiency as a function of the HF content of the carboxylic acid solution. Accordingly, the graph depicts the most unusually precipitous rise in extraction efficiency rate experienced in reducing the HF content to about 60%.

As mentioned previously, a virtual myriad of water immiscible organic solvents serve to extract IBA from aqueous HF solutions thereof in accordance with this invention. Representative suitable solvents include the aliphatic and alicyclic hydrocarbons such as the pentanes, hexanes, heptanes, cyclohexane, methyl cyclohexane and decalin. Representative aromatic hydrocarbons suitable for this purpose include benzene and the alkylated benzenes such as toluene, the various xylenes, etc. The applicable chlorinated hydrocarbons in addition to the above noted, include such as methylene chloride, chloroform, carbon tetrachloride, mono- or poly- chlorinated ethene or like ethene derivatives. Further suitable chlorinated hydrocarbons are such as the chlorinated aromatics; e.g., monochlorobenzene and the like. The chlorinated solvents are preferred due to their exceptionally low water solubility thereby minimizing HF extractability. While only a single extraction operation has been exemplified herein, the more sophisticated extraction operations such as employed in the liquid-liquid extraction technique for recovering metal values from dilute aqueous solutions can be used with advantage. Typically such an operation features countercurrent flow of the organic and aqueous phases employing a battery of extraction units.

A cyclic process for carbonylating propylene in 80% aqueous HF is schematically shown in FIG. 2. This schematic further serves to illustrate the recovery of the aqueous HF for recycling in accordance with this invention. In effecting the carbonylation reaction referred to therein, 42 g. of propylene (1.0 mole) were slowly pumped against about 190 atmospheres of carbon monoxide to a charge containing 75 g. water (4.16 moles) and 300 g. HF (15 moles) at 87°–92° C. while continuously repressuring with carbon monoxide to maintain 185-190 atmospheres. A selectivity to IBA of 97% was attained in 43 minutes. The composition of the resultant reaction mixture is as shown in the schematic. This product is thereupon distilled to provide 250 g. anhydrous HF for direct recycle to the carbonylation reactor. As shown in the schematic, a distillation residue is provided having the composition noted therein. Since 18 g. of water were consumed in the reaction, a make-up of this amount of water is eventually needed in order to provide 80% aqueous HF in the carbonylation reactor. In the absence of this make-up water, the distillation residue contains about 47% aqueous HF. In view of the fact that the extraction efficiency is somewhat higher at a lower HF concentration, it is preferred to add the requisite water to the residue prior to extraction as shown in the schematic. The water enriched residue is then extracted with an equal volume of perclene in a single extraction to provide an aqueous layer having the composition noted, which is then recycled to the carbonylation reaction. The organic layer essentially constitutes a solution of IBA in perclene and is then distilled to recover the product.

We claim:

1. In a method for the recovery of isobutyric acid prepared by the carbonylation of propylene in a reaction medium of about 80% hydrogen fluoride and 20% water; the improvement comprising distilling the resultant carbonylation reaction mixture to remove anhydrous hydrogen fluoride to the extent whereby the residual hydrogen fluoride content of said reaction medium is between about 60 and 35% and thereupon extracting the isobutyric acid content thereof with an immiscible organic solvent.

2. The improvement in accordance with claim 1 wherein the hydrogen fluoride content of said distilled reaction medium is between about 50 and 40%.

3. The improvement in accordance with claim 2 wherein said solvent is a chlorinated hydrocarbon.

4. The improvement in accordance with claim 3 wherein said chlorinated hydrocarbon is perchloroethylene.

* * * * *